United States Patent [19]

Haas et al.

[11] 4,402,681

[45] Sep. 6, 1983

[54] ARTIFICIAL IMPLANT VALVE FOR THE REGULATION OF INTRAOCULAR PRESSURE

[76] Inventors: Joseph S. Haas, 124 Green-Leaf Ave., Evanston, Ill. 60202; Gholam A. Peyman, 535 N. Michigan Ave., Apt. 3001, Chicago, Ill. 60601

[21] Appl. No.: 300,936

[22] Filed: Sep. 10, 1981

Related U.S. Application Data

[63] Continuation-in-part of Ser. No. 143,000, Aug. 23, 1980, abandoned.

[51] Int. Cl.³ ............................................. A61M 5/00
[52] U.S. Cl. ........................................ 604/9; 604/175
[58] Field of Search .............. 128/1 R, 305 R, 350 V, 128/347, 274; 137/848, 846, 849; 604/8, 9, 35, 36, 93, 117, 175, 294, 297, 256

[56] References Cited

U.S. PATENT DOCUMENTS

| | | | |
|---|---|---|---|
| 733,152 | 7/1903 | Chisholm | 128/350 V |
| 3,159,161 | 12/1964 | Ness | 604/8 |
| 3,441,160 | 4/1969 | Levy | 137/848 |
| 3,788,327 | 1/1974 | Donowitz et al. | 128/350 R |
| 4,037,604 | 7/1977 | Newkirk | 128/350 V |
| 4,153,058 | 5/1979 | Nehme | 128/347 |
| 4,331,130 | 5/1982 | Lewicky | 128/1 R |
| 4,340,037 | 7/1982 | Lewicky | 128/1 R |

OTHER PUBLICATIONS

"Filtering Valve Implant Surgery for Eyes with Neovascular Glaucoma", *Amer. Journal of Opthalmology*, Krupin et al., vol. 89, No. 3, pp. 338-343, Mar. 1980.
"Valve Implants in Filtering Surgery", *Amer. Journal of Ophthalmology*, vol. 81, No. 2, pp. 232-235, 2/76.
"An Experimental Aqueous Shunt for the Regulation of Intraocular Pressure", *Canadian Journal of Ophthalmology*, Peymen et al., vol. 9, pp. 463-467, 10/74.
"A Needle-Vent Safeguard Against Systemic Air Embolus in Open Heart Surgery", *The Journal of Thoracic Cardiovascular Surgery*, Graves et al., vol. 47, pp. 349-355, 3/64.

*Primary Examiner*—Richard J. Apley
*Assistant Examiner*—J. L. Kruter
*Attorney, Agent, or Firm*—Thomas A. Kmiotek

[57] ABSTRACT

An ophthalmic surgical valve implant apparatus for the control and relief of elevated intraocular pressure, by controlled and regulated drainage of intraocular fluid from the eye of a mammal to surrounding anatomical structures, which provides and assures proper and natural positioning of the drainage valve implant apparatus in the eye, encouraging comfortable and diffuse drainage.

6 Claims, 4 Drawing Figures

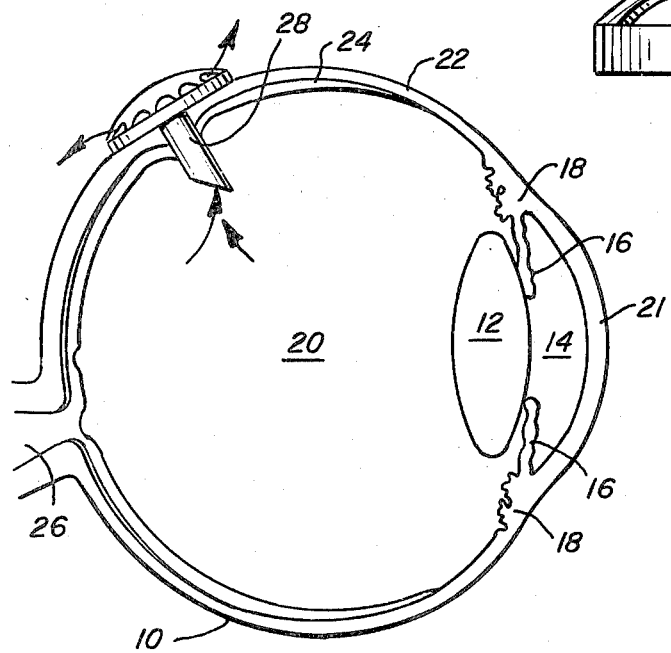
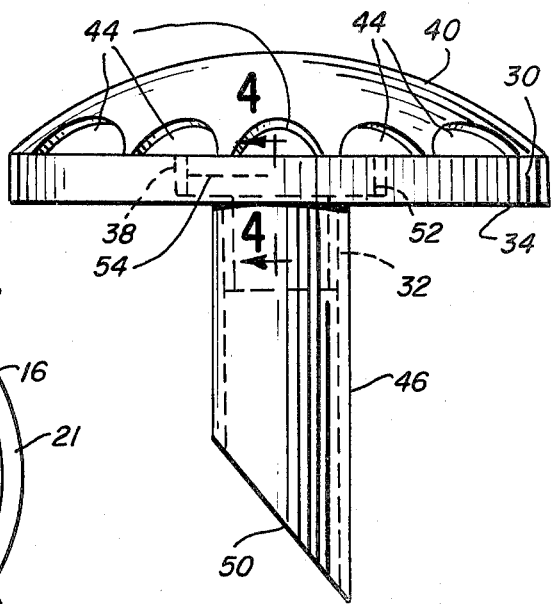
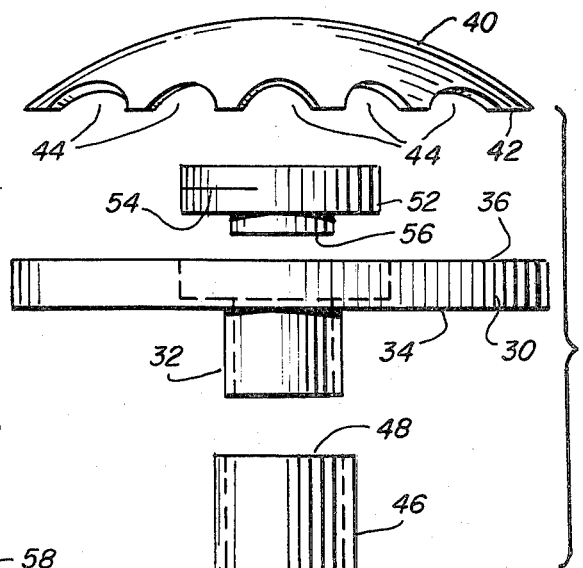
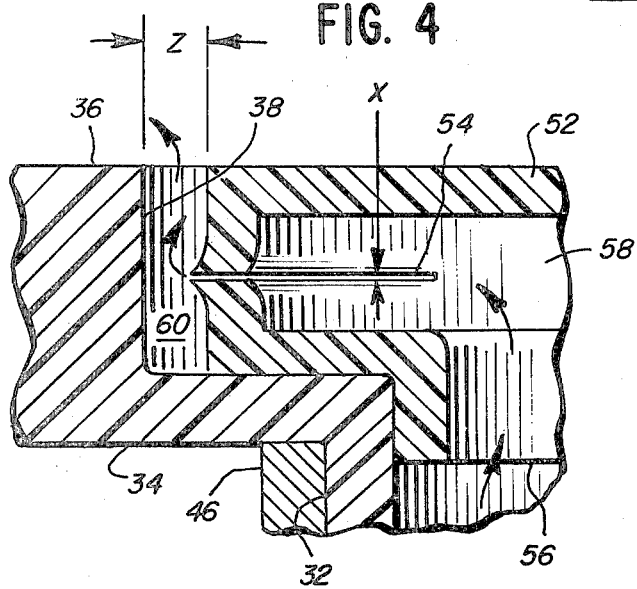

ARTIFICIAL IMPLANT VALVE FOR THE REGULATION OF INTRAOCULAR PRESSURE

RELATED APPLICATION

This is a continuation-in-part of copending application Ser. No. 143,000, filed Aug. 23, 1980, now abandoned.

FIELD OF THE INVENTION

This invention relates generally too an ophthalmic surgical valve implant apparatus. It particularly relates to an artificial implant valve and method for the control and relief of elevated intraocular pressure. The valve regulates the drainage of intraocular fluid from the eye of a mammal to the surrounding anatomical structures.

BACKGROUND OF THE INVENTION

Intraocular pressure is maintained by the circulation, within the eye, of a watery substance known as the aqueous humor. The aqueous humor is formed by the ciliary processes and passes through the pupil into the anterior chamber of the eye and out of the eye via the trabeculum Canal of Schelemm. The vitreous humor-thinly gelatinous and demonstrating very low metabolism-fills the posterior segment comprising the majority of the eye's volume.

Glaucoma is the name applied to a group of diseases characterized by an increase in the intraocular pressure of the eye, which cause atrophy of the optic nerve with resultant gradual loss of vision and, if untreated, eventual blindness. The elevation of the intraocular pressure is caused by an inability to eliminate, at an adequate rate, the aqueous humor formed by the ciliary processes of the eye. As the pressure within the eye rises, the blood supply to the optic nerve is hindered and vision is reduced. Resultant damage to the optic nerve is irreversible.

Glaucoma can often be controlled by medication that increases the drainage of the aqueous humor, such as the para-sympathetomimetics, or by medication that reduces the inflow of aqueous humor, such as the carbonic anhydrase inhibitors or the sympathetomimetics. If the administration of medication fails to control the intraocular pressure, it becomes necessary surgically to create an artifical drainage system using the patient's own tissue. This is accomplished by creating a hole in the sclera through which the aqueous humor can drain into the subconjunctival space.

Artificial implant devices comprising, either a drainage tube or a needle, and valve means, have heretofore been inserted into the anterior chamber of the eye to drain the intraocular fluid into the extraocular space beneath Tenon's capsule, in an attempt to relieve elevation of intraocular pressure. Several articles in the medical literature have disclosed artificial implant devices for the drainage of intraocular fluid. See, Peyman, et al., "An Experimental 'Aqueous Shunt' for the Regulation of Intraocular Pressure," *Canadian Journal of Ophthalmology* Vol. 9, 463–67 (October 1974) (disclosing an artificial valve for draining the anterior chamber of the eye into the subconjunctival space); Krupin, et al., "Value Implants in Filtering Surgery", *American Journal of Ophthalmology*, Vol. 81, No. 2, 232–35 (February 1976) (disclosing an artificial valve implant connecting the anterior chamber of the eye to an intrascleral pocket); and Krupin, et al., "Filtering Value Implant Surgery For Eyes with Neovascular Glaucoma," *American Journal of Ophthalmology*, Vol. 89, No. 3, 338–43 (March 1980). (diclosing the use of their artificial implant in treating neovascular glaucoma).

Prior art artificial valve implants such as described in the above-noted literature have generally comprised valves seated in tubular housings connected to hollow needles of generally circular cross section. The tube of the needle is generally either linear or curved with radii to fit the shape of the eye, and designed for insertion of the needle portion into the anterior chamber of the eye. The curved generally circular cross section hollow needles of the prior art artificial valve implants better conform those implants for placement in a plane parallel to and in closer proximity with the plane of the ocular surface formed by the lens and the iris.

The presently used, prior art ophthalmic valve implant devices generally have been designed and constructed for insertion into the anterior chamber, necessarily requiring correspondingly fine valves and fine hollow needles. Presently used ophthalmic valve implant devices, because of their restricted use in draining the anterior chamber, drain the aqueous humor to the limbus. Drainage of the aqueous humor to the limbus is usually undesirable because the limbus is frequently scarred from previous medication or surgery, and/or may be inflamed, making drainage difficult. The anterior chamber itself is a small space between the iris and the cornea. The anterior chamber can be extremely shallow or even absent, making placement of the needle difficult or impossible. Consequently, the hollow needle often comes in contact with the iris or the cornea so that the lumen of the needle can become plugged. If a surgeon attempts to insert the hollow needle of the known valve implant devices at other anatomical sites in the eye by bending the needle, the lumen of the needle can become kinked and occluded, therefore hindering or preventing drainage of the aqueous humor through the valve implant device.

Presently available valve implant devices also generally require an extra surgical step of first piercing the eye before insertion of the valve implant.

Ophthalmic valve implant devices incorporating double reed type valves in their design are also known and are currently used. A particular disadvantage of these valves is the imprecise and relatively difficult regulation of the opening pressure of the valve.

Existing valve implant devices of unitary construction which may be implanted into the posterior chamber exhibit numerous problems. Material choice may be limited since one material has to function as a valve and stem portion requiring flexibility (for the valve) and rigidity (for the stem) simultaneously. Barbs, anchoring sutures or other fastening means existing in prior art implant valves are also necessary to secure the implant valves to the eye. Existing valve implant devices also only drain fluid to surrounding anatomical structures through a single channel. If the single channel becomes occluded drainage can be severely impeded or stopped altogether.

The critical lack in the art of ophthalmic surgical valve implant apparatus specifically designed for insertion in and drainage of the posterior chamber of the eye is apparent. As a result, there is a need in the art for an ophthalmic surgical valve implant apparatus which is specifically designed for use in draining the posterior chamber or segment of an eye afflicted with glaucoma. The optimal anatomical site for drainage when the limbus is scarred or inflamed is the posterior segment or chamber of the eye. Surgical creation of a hole in the sclera with the patient's own tissue through which the aqueous humor can drain into the subconjunctival space is far less desirable than using an ophthalmic surgical valve implant affording insertion into the posterior segment or chamber of the dye, which would further obviate drainage to a scarred, surgically altered or inflamed limbus.

Insertion into the posterior segment or chamber of the eye of an ophthalmic surgical valve implant apparatus better conforming to the natural curvature of the eye would obviate the need to anchor the implanted valve using sutures, barbs or other fastening means, since the conforming shape would be less likely to work loose after implanting. Furthermore, a valve implant of distinct and separate elemental construction, rather than unitary construction, eliminates some of the afore-noted material problems associated with the known unitary microfine valves.

The art also lacks an ophthalmic surgical valve implant apparatus capable of drainage through an array of discharge perforations, which would minimize the occluding of a single drainage channel. Also lacking in the art is a self-piercing ophthalmic valve implant device that eliminates the first surgical step of separately piercing the eye before insertion. Finally, easier and more precise regulation of valve opening pressure is needed than can be accomplished using the known double reed type valves.

SUMMARY OF THE INVENTION

The present invention overcomes the drawbacks of the prior art by providing an ophthalmic surgical valve implant apparatus and method for the control and relief of elevated intraocular pressure, by controlled and regulated drainage of intraocular fluid from the eye of a mammal to surrounding anatomical structures without extensive surgical preparations, which provides and assures proper and natural positioning of the drainage valve implant apparatus in the eye, encouraging comfortable and diffuse drainage.

Accordingly, it is an object of this invention to provide an ophthalmic surgical valve implant apparatus which is not restricted to use in draining the anterior chamber of an eye afflicted with glaucoma, but which can be inserted into any part of the eye that provides an optimal anatomical site for drainage, including the posterior segment or chamber of the eye.

It is a further object of this invention to provide an ophthalmic surgical valve implant apparatus which can be inserted without the initial separate and additional step of surgical creation of an incision in the eye for the valve implant apparatus.

It is another object of this invention to provide an ophthalmic surgical implant apparatus whose configuration assures anchoring after surgical implanting thereby obviating the separate and additional step of suturing the valve implant apparatus to the eye or requiring barbs or other fastening means on the apparatus to anchor it into position.

It is another object of this invention to provide an ophthalmic valve implant apparatus that can be naturally positioned in the eye having a perforated crown configuration conforming to the natural curvature of the eye, thereby encouraging comfortable and diffuse drainage through an array of perforations and minimizing the probability of occluding the drainage channel.

It is another object of this invention to provide a method for draining the intraocular fluid from the vitreous cavity of an eye by insertion of a novel and improved ophthalmic surgical valve implant apparatus of this invention into the posterior segment or chamber of the eyeball at a point where a pocket of fluid vitreous or aqueous is present or has been provided by performing a partial vitrectomy.

It is another object of this invention to provide an ophthalmic valve implant apparatus of distinct and separate elemental microfine construction thereby eliminating material problems associated with the known unitary microfine valves whereby the optimal material for each element can be chosen to be compatible with the function performed by the particular element.

It is another object of this invention to provide an ophthalmic valve implant apparatus having an easily and precisely regulatable slit valve.

The present invention comprises an ophthalmic surgical valve implant apparatus and method for the control and relief of elevated intraocular pressure by controlled and regulated drainage of intraocular fluid from the eye of a mammal to surrounding anatomical structures. The implant device comprises a hollow needle means which is inserted into the eye. A valve housing means is attached to said needle means. The valve housing means has a hollow stem fixedly attached thereto or integrally formed therewith and a receiving means with a fluid passage extending from said receiving means through the stem to said hollow needle means. The hollow stem of the valve housing means and the hollow needle means are concentrically interlocked, thereby attaching the hollow needle means to the valve housing means. The valve housing means and the hollow needle can also be integrally formed. A pressure dependent slit valve means is fixedly located in the receiving means of the valve housing means so as to regulate intraocular fluid flow from the eye. A generally hollow crown covers and is attached to the valve face of the valve housing means, which face is disposed opposite to the stem. An array of perforations at the peripheral intersection edge of the generally hollow crown and the valve face allows drainage of the intraocular fluid to the tissues surrounding the eye. The generally hollow crown can also be constructed of a substantially rigid mesh-type framework or other rigid pervious material, or otherwise can be provided with at least one perforation at some location on its surface.

The ophthalmic surgical valve implant apparatus of this invention is designed to be inserted into any part of the eye that provides an optimal anatomical drainage site. When the ophthalmic valve implant device of this invention is inserted into the posterior segment or chamber of the eye, ease of insertion and fixed placement is assured. The hollow needle portion of the ophthalmic valve implant apparatus incises the eye as the device is inserted so that a separate incision followed by insertion of the device is not necessary. The slit valve means seated in the receiving means of the valve housing may be a unidirectional pressure dependent slit valve. The slit valve means is designed to close at a few mm Hg below normal intraocular pressure, and it is designed to open at approximately normal intraocular pressure or above. The range of opening and closing pressures may also be chosen to maintain intraocular pressure within a prescribed range. Use of a slit valve allows more precise and easier regulation of opening pressures than double reed type valves since opening pressure can be adjusted or controlled by the length of the slit in the valve.

The generally hollow crown of the apparatus is dome shaped and designed to conform to the natural curvature of the eye at the placement site. The valve face of the valve housing means disposed adjacent the stem additionally can be shaped to conform to the natural curvature of the eye at the placement site. At instances when the intraocular pressure is elevated above an acceptable pressure, the intraocular fluid will drain from the eye through the hollow needle, through the unidirectional pressure dependent valve, to the hollow cavity of the generally hollow crown, and from the cavity of the generally hollow crown through one or more perforations into the surrounding tissue. Use of an array of perforations at the point of discharge to surrounding anatomical structures, particularly at the peripheral intersection edge of the crown and the valve face, minimizes the probability of occluding a single drainage channel. In the instance of insertion of the valve into the posterior segment or chamber of the eye, the intraocular fluid will drain from the vitreous cavity into the loose connective tissue of the muscle cone. If a pocket of fluid vitreous or aqueous is not present at the point of insertion into the posterior segment or chamber, a partial vitrectomy can be performed at the site of insertion of the hollow needle portion of said ophthalmic surgical valve implant apparatus to provide such a pocket within the eye.

Concentric alignment of the valve housing and the stem and hollow needle is not necessary for this invention to function. Indeed, situations may dictate that the stem and the hollow needle be placed eccentrically with respect to the valve housing.

Other objects and advantages of this invention will become apparent upon reading the following detailed description and appended claims.

BRIEF DESCRIPTION OF THE DRAWINGS

For a more complete understanding of this invention reference should now be had to the embodiment illustrated in greater detail in the accompanying drawings.

In the drawings:

FIG. 1 is a cross-sectional view of the eye of a mammal showing the ophthalmic valve implant apparatus of this invention inserted into the posterior segment of the eye.

FIG. 2 is a side view of the ophthalmic valve implant apparatus of this invention.

FIG. 3 is a side view of the elemental development of the ophthalmic valve implant apparatus of this invention.

FIG. 4 is a partial cross section, taken at Section 4—4 as shown in FIG. 2, of the ophthalmic valve implant apparatus of this invention showing the unidirectional valve seated in the apparatus.

DESCRIPTION OF THE PREFERRED EMBODIMENT

Turning first to FIG. 1, there is shown an eye of a mammal 10 which includes a lens 12, an anterior chamber 14, an iris 16, a ciliary body 18, a cornea 21, a sclera 22, a choroid-retina 24 and an optic nerve 26 of the eyeball 10. As shown in the figure, an ophthalmic valve implant apparatus 28 of the present invention when surgically implanted into the eye pierces the slcera 22 and the choroid-retina 24 to extend into the posterior segment 20 of the eye.

With reference now to FIGS. 2 and 3, a particularly preferred embodiment of the ophthalmic valve implant apparatus of the invention is illustrated in more detail, depicting a valve housing means 30 which is generally circular and disk-like in shape having an outwardly directed hollow circular mounting stem 32 attached to or formed as a part of an inner facing side 34 of said housing means 30. The valve housing means also has an outer facing side 36 and a circular receiving means 38 in said side. A generally hollow crown 40 having a circular base 42 is mounted and fixed to the outer facing side 36 of the valve housing means 30. The generally hollow crown 40, has, in spaced array, a plurality of perforations 44 adjacent the intersection of the circular base 42 of the hollow crown 40 and the outer facing side 36 of the valve housing means 30.

In accordance with this invention, FIGS. 1, 2 and 4 are illustrative of the operation of the ophthalmic valve implant. FIG. 1 shows the surgical implantation of the ophthalmic valve implant apparatus 28 in the posterior segment 20 of the eye. Surgical implantation is accomplished by merely piercing the sclera 22 and choroid retina 24 with the sharpened penetrant end 50 of the apparatus in order that the hollow needle 46 projects a sufficient distance into the posterior segment 20 to allow drainage of the fluid vitreous or aqueous contained therein. The inner facing side 34 of the valve housing means 30 abuts the outside of the sclera 22.

Generally, the ophthalmic valve implant apparatus 28 of this invention will be inserted into the posterior segment 20 where a pocket of fluid vitreous or aqueous is present. The vitreous is a clear, avascular, gelatinous body which comprises two-thirds of the volume and weight of the eye. It fills the space bounded by the lens, retina, and optic disk. Like all types of gel, the vitreous, with the passage of time, can degenerate and form fluid-filled cavities. Fluid vitreous or aqueous can fill these cavities. Absent a pocket of fluid vitreous or aqueous at the selected anatomical implant site into the posterior segment, a partial vitrectomy can be performed by the surgeon implanting the apparatus. Partial vitrectomy involves microsurgically removing less than all of the vitreous and replacing it by saline. The partial vitrectomy will create a permanent pocket of fluid vitreous or aqueous allowing internal ophthalmic pressure to be relieved by drainage from the pocket.

Fluid vitreous or aqueous will only drain from the eye when intraocular pressure is elevated above normal. In this situation the partial circumferential slit 54 of slit valve means 52 opens to a width X shown in FIG. 4. allowing fluid vitreous or aqueous to flow through the hollow needle 46 through said slit valve means 52 and into a cavity 58 therein. Thereafter fluid vitreous or aqueous flows through the opening X of the slit 54 to the annular duct 60 of width Z for passage to the cavity created between the hollow crown 40 and the outside face 36 of the valve housing.

The hollow needle 46 with a flat end 48 and the sharpened penetrant end 50 is fixedly attached concentrically over the hollow circular mounting stem 32 so that the flat end 48 abuts the inner facing side 34 of the valve housing means 30.

In an alternative embodiment the valve housing means 30 and the needle 46 are one integral component obviating the need for a hollow mounting stem.

A unidirectional circular slit valve means 52 having a partial circumferential slit 54 and a portal opening 56 in the bottom of said valve is fixedly mounted or seated in the circular receiving means 38 of the valve housing means 30. The arc traced by the circumferential slit 54 determines the opening and closing pressure for the slit valve means 52. FIG. 4 is a partial cross section of the apparatus of the invention taken at 4—4 (FIG. 2) showing the slit valve means 52. An annular duct 60 of width Z is shown to exist between the peripheral edge of the slit valve 52 and the wall defining the receiving means 38.

The array of perforations 44 allows drainage to the tissues surrounding the eye 10. The crown 40 itself is a configuration which closely conforms to the natural curvature of the eye encouraging comfortable and diffuse drainage. When intraocular pressure is within a normal range, the slit valve closes and the opening X disappears.

While a particular embodiment of the invention has been shown, it will be understood, of course, that the invention is not limited thereto since modification may be made by those skilled in the art, particularly in light of the foregoing teachings. It is, therefore, contemplated by the appended claims to cover any such modifications as incorporate those features which constitute the essential features of these improvements within the true spirit and the scope of this invention.

We claim:

1. An ophthalmic valve implant apparatus whereby elevated intraocular pressure is relieved by regulating the drainage of intraocular fluid from the eye of a mammal comprising:

a hollow needle for insertion into the eye;
    a generally disk-shaped valve housing means having an outer facing side, an inner facing side, a receiving means in the outer facing side, a hollow stem projecting outwardly from said inner facing side, said housing means having a fluid passage extending from said receiving means into said hollow stem, said hollow stem being concentrically interlocked to said hollow needle;
    a unidirectional, pressure dependent slit valve means fixedly located within said receiving means of said valve housing means whereby intraocular fluid drains from the eye, when the intraocular pressure becomes elevated, through said hollow needle, through said hollow stem, and through said slit valve means to exit said slit valve means proximate to said outer facing side of said valve housing means; and,
    a generally hollow crown having a substantially circular base and a dome substantially conforming to the natural curvature of the eye, said base being affixed to said outer facing side of said valve housing means, whereby a cavity intermediate said crown and said outer facing side of said valve housing means is formed, said generally hollow crown having at least one perforation therein at the juncture of said base and said outer facing side of said valve housing means for drainage of intraocular fluid.

2. The ophthalmic surgical valve implant apparatus of claim 1 wherein said hollow stem and said valve housing means are integral.

3. The ophthalmic surgical valve implant apparatus of claim 1 wherein said inner facing side of said valve housing means substantially conforms to the natural curvature of the eye.

4. The ophthalmic surgical valve implant apparatus of claim 2 wherein said inner facing side of said valve housing means substantially conforms to the natural curvature of the eye.

5. An ophthalmic valve implant apparatus whereby elevated intraocular pressure is relieved by regulating the drainage of intraocular fluid from the eye of a mammal comprising:

a hollow needle for insertion into the eye;
    a generally disk-shaped valve housing means having an outer facing side, an inner facing side substantially conforming to the natural curvature of the eye, a receiving means in the outer facing side, a hollow stem projecting outwardly from said inner facing side, said housing means having a fluid passage extending from said receiving means into said hollow stem, said hollow stem being concentrically interlocked to said hollow needle;
    a unidirectional, pressure dependent slit valve means fixedly located within said receiving means of said valve housing means whereby intraocular fluid drains from the eye, when the intraocular pressure becomes elevated, through said hollow needle, through said hollow stem, and through said slit valve means to exit said slit valve means proximate to said outer facing side of said valve housing means; and,
    a generally hollow crown having a substantially circular base and a dome substantially conforming to the natural curvature of the eye, said base being affixed to said outer facing side of said valve housing means, whereby a cavity intermediate said crown and said outer facing side of said valve housing means is formed, said generally hollow crown having at least one perforation therein for drainage of intraocular fluid.

6. The ophthalmic surgical valve implant apparatus of claim 5 wherein said hollow stem and said valve housing means are integral.

* * * * *